US006833446B1

(12) United States Patent
Wood et al.

(10) Patent No.: US 6,833,446 B1
(45) Date of Patent: Dec. 21, 2004

(54) COMPOSITIONS AND METHODS FOR THE MODIFICATION OF GENE TRANSCRIPTION

(75) Inventors: Marion Wood, Auckland (NZ); Michael A. Shenk, Auckland (NZ); Annette McGrath, Auckland (NZ); Matthew Glenn, Parnell (NZ)

(73) Assignees: Agrigenesis Biosciences Limited, Auckland (NZ); Rubicon Forest Holdings Limited, Auckland (NZ)

( * ) Notice: Subject to any disclaimer, the term of this patent is extended or adjusted under 35 U.S.C. 154(b) by 142 days.

(21) Appl. No.: 09/640,211

(22) Filed: Aug. 16, 2000

Related U.S. Application Data

(63) Continuation of application No. PCT/US00/06112, filed on Mar. 9, 2000, and a continuation-in-part of application No. 09/266,513, filed on Mar. 11, 1999, now abandoned.
(60) Provisional application No. 60/149,485, filed on Aug. 18, 1999.

(51) Int. Cl.$^7$ .................. C07H 21/00; C07H 21/04; C12N 1/20; C12N 5/00

(52) U.S. Cl. .................. 536/22.1; 536/23.1; 435/252.3; 435/325

(58) Field of Search .................. 536/23.1, 22.1; 435/252.3, 325

(56) References Cited

U.S. PATENT DOCUMENTS

| 4,683,202 A | * | 7/1987 | Mullis .................. 435/91.2 |
| 5,907,082 A | | 5/1999 | O'Neill et al. .................. 800/205 |

FOREIGN PATENT DOCUMENTS

| AU | 3901395 | 11/1995 | ........... C12N/15/29 |
| WO | 9314211 | 7/1993 | ........... C12N/15/82 |
| WO | 9635784 | 11/1996 | ........... C12N/15/12 |
| WO | 9813503 | 4/1998 | ........... C12N/15/82 |
| WO | 9822592 | 5/1998 | ........... C12N/15/29 |
| WO | 9854328 | 12/1998 | ........... C12N/15/29 |

OTHER PUBLICATIONS

Uimari et al., "Myb26: a MYB–like protein of pea flowers with affinity for promoters of pheylpropaniod genes", The Plant Journal, vol. 12, No. 6, pp. 1273–1284 (1997).*
Uimari et al., Accession No. Y11105, Plant Physiol., 117, 720 (1998).*
Jackson, David, et al., "Expression Patterns of myb Genes from Antirrhinum Flowers," The Plant Cell, Feb. 1991, pp. 115–125, vol. 3.
PCT International Search Report; In re Genesis Research and Development Corporation, Ltd.; International Application No. PCT/US00/06112, filed Mar. 9, 2000.
GenBank Accession No. AF029975, submitted Nov. 19, 1998.
GenBank Accession No. T42925, submitted Nov. 6, 1997.
GenBank Accession No. AF1581543, submitted Dec. 16, 1999.
GenBank Accession No. AW394752, submitted Jul. 17, 2000.
GenBank Accession No. AW010840, submitted Sep. 10, 1999.
GenBank Accession No. AF120097, submitted Feb. 1, 2000.
GenBank Accession No. U90348, submitted Oct. 10, 1997.
GenBank Accession No. AW587800, submitted Mar. 22, 2000.
GenBank Accession No. AI812413, submitted Jul. 8, 1999.
GenBank Accession No. AW226013, submitted Dec. 10, 1999.
GenBank Accession No. U90091, submitted Jan. 5, 1999.
GenBank Accession No. U90092, submitted Jan. 5, 1999.
GenBank Accession No. X69899, submitted Nov. 24, 1993.
GenBank Accession No. AW399147, submitted Feb. 7, 2000.
GenBank Accession No. AA867891, submitted Aug. 28, 1998.
GenBank Accession No. AF086642, submitted Apr. 8, 1999.
Zhang, Bei et al, "Isolation and characterization of two related Arabidopsis ocs–element bZIP binding proteins", Plant Journal, vol. 4, No. 4, pp. 711–716 (1993).
Tandre, Karolina et al., "Conifer homologues to genes that control floral development in angiosperms", Plant Molecular Biology, vol. 27, pp. 69–78 (1995).
Sundstrom, Jens et al., "MADS–Box Genes Active in Developing Pollen Cones of Norway Spruce (picea abics) Are Homologous to the B–Class Floral Homeolic Genes in Angiosperms", Developmental Genetics, vol. 25, pp. 253–266 (1999).
Perrey, Ralph et al., "Molecular cloning of a luOpin–specific gene from a cDNA library of suspension–cultured cells of Lupinus polyphyllus ", Plant Molecular Biology, vol. 15, pp. 175–176 (1990).
Newman, Tom et al., "Genes Galore; A summary of Methods for Accessing Results from Large–Scale Partial Sequencing of Anonymous Arabidopsis cDNA Clones", Plant Physiol., vol. 106, pp. 1241–1255 (1994).
Ma, Hongchang et al., "Identification of a homeobox–containing gene with enhanced expression during soybean (Glycine max L.) somatic embryo development", Plant Molecular Biology, vol. 24, pp. 465–473 (1994).
Kawahara, Ryoichi et al., "Isolation and characterization of homeobox–containing genes of carrot", Plant Molecular Biology, vol. 27, pp. 155–164 (1995).

(List continued on next page.)

Primary Examiner—Ethan Whisenant
Assistant Examiner—Joyce Tung
(74) Attorney, Agent, or Firm—Ann W. Speckman; Janet Sleath

(57) ABSTRACT

Novel isolated polynucleotides that encode plant transcription factors are provided, together with DNA constructs comprising such polynucleotides. Methods for using such constructs in modulating the expression of endogenous and/or heterologous genes are also disclosed, together with transgenic plants comprising such constructs.

14 Claims, No Drawings

OTHER PUBLICATIONS

Southerton, Simon G. et al., "Eucalypt MADS–Box Genes Expressed in Developing Flowers", *Plant Physiol.*, vol. 118, pp. 365–372 (1998).

Schena, Mark and Davis, Ronald W., "HD–Zip proteins: Members of an Arabidopsis homeodomain protein superfamily", *Proc. Natl. Acad. Sci.*U.S.A., vol. 89, pp. 3894–3898 (May, 1992).

Bradley, Desmond et al., "Complementary Floral Homeotic Phenotypes Result from Opposite Orientations of a Transposon at the plean Locus of Antirrhinum", *Cell*, vol. 72, pp. 85–95 (Jan. 1993).

Valle, Estela M., et al., "Isolation and expression pattern of huhr 1, a homeobox–containing cDNA from *Helianthus annuus*", *Gene*, vol. 196, pp. 61–68 (1997).

* cited by examiner

US 6,833,446 B1

COMPOSITIONS AND METHODS FOR THE MODIFICATION OF GENE TRANSCRIPTION

CROSS-REFERENCE TO RELATED APPLICATIONS

This application is a continuation and claims priority to International Patent Application No. PCT/US/00/06112, filed Mar. 9, 2000, and U.S. Provisional Patent Application No. 60/149,485, filed Aug. 18, 1999, and is a continuation-in-part of U.S. patent application Ser. No. 09/266,513, filed Mar. 11, 1999 now abandoned.

TECHNICAL FIELD OF THE INVENTION

This invention relates to compositions isolated from plants and their use in the modification of gene transcription and/or expression. More specifically, this invention relates to plant polynucleotide sequences encoding transcription factors that are components of the cellular transcription apparatus and the use of such polynucleotide sequences in the modification of gene expression.

BACKGROUND OF THE INVENTION

Eucaryotic gene expression is regulated, in part, by the cellular processes involved in transcription. During transcription, a single-stranded RNA complementary to the DNA sequence to be transcribed is formed by the action of RNA polymerases. Initiation of transcription in eucaryotic cells is regulated by complex interactions between cis-acting DNA motifs, located upstream of the gene to be transcribed, and trans-acting protein factors. Among the cis-acting regulatory regions are sequences of DNA, termed promoters, which are located close to the transcription initiation site and to which RNA polymerase is first bound, either directly or indirectly. Promoters usually consist of proximal (e.g., TATA box) and more distant elements (e.g., CCAAT box). Enhancers are cis-acting DNA motifs which may be situated further up- and/or down-stream from the initiation site.

Both promoters and enhancers are generally composed of several discrete, often redundant, elements each of which may be recognized by one or more trans-acting regulatory proteins, known as transcription factors. Regulation of the complex patterns of gene expression observed both spatially and temporally, in all developing organisms, is thought to arise from the interaction of enhancer- and promoter-bound, general and tissue-specific transcription factors with DNA (Izawa T, Foster R and Chua N H, *J. Mol. Biol.* 230:1131–1144, 1993; Menkens A E, Schindler U and Cashmore A R, *Trends in Biochem. Sci.* 13:506–510, 1995). Developmental decisions in organisms as diverse as *Drosophila melanogaster, Saccharomyces cerevisiae, Arabidopsis thaliana* and *Pinus radiata* are regulated by transcription factors. These DNA-binding regulatory molecules have been shown to control the expression of genes responsible for the differentiation of different cell types, for example, the differentiation of leaf trichomes and xylem tissue in *Arabidopsis thaliana,* formation of endoderm from embryonic cells in *Xenopus laevis* and the initiation of gene expression in response to environmental and phytohormonal stress in plants (Yanagisawa S and Sheen J, *The Plant Cell* 10:75–89, 1998).

Transcription factors generally bind DNA in a sequence-specific manner and either activate or repress transcription initiation. The specific mechanisms of these interactions remain to be fully elucidated. At least three separate domains have been identified within transcription factors. One is essential for sequence-specific DNA recognition, one for the activation/repression of transcriptional initiation, and one for the formation of protein-protein interactions (such as dimerization). Four motifs, or domains, involved in DNA sequence recognition and/or transcription factor dimerization have been identified to date: zinc fingers; helix-turn-helix; leucine zipper; and helix-loop-helix. Both helix-loop-helix and leucine zipper protein motifs have been implicated in the binding of transcription factors to DNA via their ability to readily form homo- or hetero-dimers in vivo. "Activating" domains are rich in either proline, glutamine or acidic amino acids. It has been proposed that this net negative region of the transcription factor interacts with the TATA box-binding transcription factor TFIID, RNA polymerase, and/or another protein associated with the transcription apparatus.

Studies indicate that many plant transcription factors can be grouped into distinct classes based on their conserved DNA binding domains (Katagiri F and Chua N H, *Trends Genet.* 8:22–27, 1992; Menkens A E, Schindler U and Cashmore A R, *Trends in Biochem. Sci.* 13:506–510, 1995; Martin C and Paz-Ares J, *Trends Genet.* 13:67–73, 1997). Each member of these families interacts and binds with distinct DNA sequence motifs that are often found in multiple gene promoters controlled by different regulatory signals. Several classes of transcription factors that have been identified to date are described below.

The basic/leucine zipper (bZIP) is a conserved family of transcription factors defined by a basic/leucine zipper (bZIP) motif (Landschultz et al., *Science* 240:1759–1764, 1988; McKnight, *Sci Am.* 264:54–64,1991; Foster et al., *FASEB J.* 8[2]:192–200, 1994). Transcriptional regulation of gene expression is mediated by both the bZIPs and other families of transcription factors, through the concerted action of sequence-specific transcription factors that interact with regulatory elements residing in the promoter regions of the corresponding gene. The bZIP bipartite DNA binding structure consists of a region enriched in basic amino acids (basic region) adjacent to a leucine zipper that is characterized by several leucine residues regularly spaced at seven amino acid intervals (Vinson et al., *Science* 246:911–916, 1989). Whereas the basic region directly contacts the DNA, the leucine zipper mediates homodimerisation and heterodimerisation of protein monomers through a parallel interaction of the hydrophobic dimerization interfaces of two α-helices, resulting in a coiled-coil structure (O'Shea et al., *Science* 243:538–542, 1989; *Science* 254:539–544, 1991; Hu et al., *Science* 250:1400–1403,1990; Rasmussen et al., *Proc. Natl. Acad. Sci. USA* 88:561–564, 1991).

Dof proteins are a relatively new class of transcription factor and are thought to mediate the regulation of some patterns of plant gene expression in part by combinatorial interactions between bZIP proteins and other types of transcription factors binding to closely linked sites. Such an example of this combinatorial interaction has been observed between bZIP and Dof transcription factors (Singh, *Plant Physiol.* 118:1111–1120, 1998). These Dof proteins possess a single zinc-finger DNA binding domain that is highly conserved in plants (Yanagisawa, *Trends Plant Sci.* 1:213, 1996). Specific binding of the Dof protein to bZIP transcription factors has been demonstrated and it has been proposed that this specific interaction results in the stimulation of bZIP binding to DNA target sequences in plant promoters (Chen et al., *Plant J.* 10:955–966, 1996). Examples of such Dof/bZIP interactions have been reported in the literature, including for example, the *Arabidopsis thaliana* glutathionine S-transferase-6 gene (GST6) promoter which has been shown to contain several Dof-binding sites closely linked to the ocs element, a recognized bZIP binding site (Singh, Plant Physiol. 118:1111–1120, 1998).

The bZIP family f G-box binding factors from Arabidopsis (including GBF1, GBF2 and GBF3, for example) interact with the palindromic G-box motif (CCACGTGG). However, it has been demonstrated that the DNA binding specificity of such transcription factors, for example GBF1, may be influenced by the nature of the nucleotides flanking the ACGT core (Schindler et al., *EMBO J.* 11:1274–1289, 1992a). In vivo transient and transgenic plant expression studies have shown that these ACGT elements are necessary for maximal transcriptional activation and have been identified in a multitude of plant genes regulated by diverse environmental, physiological, and environmental cues. Classification of these transcription factors based upon their ability to bind to the ACGT core motif yielded a relatively diverse group of proteins, including, for example the CamV 35S promoter as-1-binding protein which exhibits DNA binding site requirements distinct from those proteins interacting with the G-box (Tabata et al., *EMBO J.* 10:1459–1467, 1991). Thus, in addition to defining the individual classes of bZIP proteins on the basis of their DNA binding specificity, such proteins can also be classified according to their heterodimerisation characteristics (Cao et al., *Genes Dev.* 5:1538–1552, 1991; Schindler et al., *EMBO J.* 11:1261–1273, 1992b).

Environmentally inducible promoters require the presence of two cis-acting elements, critical for promoter activity, one of which is the moderately conserved G-box (CCACGTGG) (deVetten et al., *Plant Cell* 4[10]:1295–1307, 1992). A mutation in one of the two elements abolishes or severely reduces the ability of the promoter to respond to environmental changes. The sequence of the second cis-acting element, positioned near the G-box, is not conserved among different environmentally-inducible promoters, but may be similar among promoters induced by the same signal. The spacing between the G-box and the second cis-acting element appears to be critical, suggesting a direct interaction between the respective binding factors (deVetten and Ferl, *Int. J. Biochem.* 26[9]:1055–1068, 1994; Ramachandran et al., *Curr. Opin. Genet. Dev.* 4[5]:642–646, 1994).

Basic helix-loop-helix zipper proteins represent an additional class of bZIP transcription factors described in the literature and includes, for example, the Myc proteins. These proteins contain two regions characteristic of transcription factors: an N-terminal transactivation domain consisting of several phosphorylation sites, and a C-terminal basic helix-loop-helix (bHLH) leucine zipper motif known to mediate dimerization and sequence specific DNA binding via three distinct domains: the leucine zipper, helix-loop-helix, and basic regions.

The Myb family of transcription factors is a group of functionally diverse transcriptional activators found in both plants and animals that is characterized by a conserved amino-terminal DNA-binding domain containing either two (in plant species) or three (in animal species) imperfect tandem repeats of approximately 50 amino acids (Rosinski and Atchley, *J. Mol. Evol.* 46(1):74–83, 1998; Stober-Grasser et al., *Oncogene* 7[3]:589–596, 1992). Comparisons between the amino acid sequences of representative plant and mammalian MYB proteins indicate that there is a greater conservation between the same repeat from different proteins, than between the R2 and R3 repeats from the same protein (Martin and Paz-Ares, *Trends Genet.* 13[2]:67–73, 1997). More than 100 MYB genes have been reported from *Arabidopsis thaliana* (Romero et al., *Plant J.* 14[3]:273–284, 1998), representing the largest regulatory gene family currently known in plants. DNA-binding studies have demonstrated that there are differences, but also frequent overlaps, in binding specificity among plant MYB proteins, in line with the distinct but often related functions that are beginning to be recognized for these proteins. Studies involving the eight putative base-contacting residues in MYB DNA binding domains have revealed that at least six are fully conserved in all plant MYB proteins identified to date and the remaining two are conserved in at least 80% of these proteins (Martin and Paz-Ares, *Trends Genet.* 13[2]:67–73, 1997). Mutational analysis involving residues that do not contact bases have indicated that the sequence-specific binding capacity of MYBs is affected and this may account for some of the differences in the DNA-binding specificity between plant MYB proteins (Solano et al., *J. Biol. Chem.* 272[5]:2889–2895, 1997). This large-sized gene family may contribute to the regulatory flexibility underlying the developmental and metabolic plasticity displayed by plants.

Homeotic transcription factors have, in animals, been implicated in a number of developmental processes including, for example, the control of pattern formation in insects and vertebrate embryos and the specification of cell differentiation in many tissues (Ingham, *Nature* 335:25–34, 1988; McGinnis and Krumlauf, *Cell* 68:283–302, 1992). Homeodomain secondary structures are characterized by a distinctive helix-turn-helix motif initially identified in bacterial DNA binding domains. This helix-turn-helix sequence/structure motif spans approximately 20 amino acids and is characterized by two short helices separated by a sharp 90 degree bend or turn (Harrison and Aggarwal, *Ann. Rev. Biochem.* 59:933–969, 1990). This helix has been shown to bind in the major groove of the DNA helix.

Plant homeobox genes have been identified in a number of plant species including *Arabidopsis thaliana*, maize, parsley and soybean. Expression pattern analysis of maize homeobox gene family members suggests that these transcription factors may be involved in defining specific regions in the vegetative apical meristem, potentially involved in the initiation of leaf structures (Jackson et al., *Development* 120:405–413, 1994). Such observations imply that the plant homeobox genes, as for the animal homeobox genes, may be involved in the determination of cell fate.

Homeodomain-zipper (HD-zip) represents an additional family of homeodomain proteins. These homeodomain-zipper proteins (HD-zip) possess both the characteristic homeodomain linked to an additional leucine zipper dimerization motif. This family includes, for example, Athb-1 and Athb-2 (Sessa et al., *EMBO J.* 12:3507–3517, 1993) and Athb-4 (Carabelli et al., *Plant J.* 4:469–479, 1993).

The LIM domain is a specialized double-zinc finger motif found in a variety of proteins, in association with domains of divergent functions, such as the homeodomain (see the sunflower pollen-specific SF3 transcription factor: Baltz et al., *Plant J.* 2:713–721, 1992; or forming proteins composed primarily of LIM domains: Dawid et al., *Trends Genet.* 14[4]:156–162, 1998). LIM domains interact specifically with other LIM domains and with many different protein domains. LIM domains are thought to function as protein interaction modules, mediating specific contacts between members of functional complexes and modulating the activity of some of the constituent proteins. Nucleic acid binding by LIM domains, while suggested by structural considerations, remains an unproven possibility. However, it is possible that together with the homeodomain, the LIM domain could bind to the regulatory regions of developmentally controlled genes, as has been proposed for the paired box, a conserved sequence motif first identified in the paired (PRD) and gooseberry (GSB) homeodomain proteins from Drosophila (Triesman et al., *Genes Dev.* 5:594–604, 1991). The PRD box is also able to bind DNA in the absence of the homeodomain. LIM-domain proteins can be nuclear, cytoplasmic, or can shuttle between compartments. In the animal systems, several important LIM proteins have been shown to be associated with the cytoskeleton, having a role in adhesion-plaque and actin-microfilament organization. Among nuclear LIM proteins, the LIM homeodomain proteins form a major subfamily with important functions in cell lineage determination and pattern formation during animal development.

The AP2 (APETALA2) and EREBPs (ethylene-responsive element binding proteins) are the prototypic members of a family of transcription factors unique to plants, whose distinguishing characteristic is that they contain the so-called AP2 DNA-binding domain. AP2/EREBP genes form a large multigene family, and they play a variety of roles throughout the plant life cycle: from being key regulators of several developmental processes, like floral organ identity determination or control of leaf epidermal cell identity, to forming part of the mechanisms used by plants to respond to various types of biotic and environmental stress. In *Arabidopsis thaliana*, the homeotic gene APETALA2 (AP2) has been shown to control three salient processes during development: (1) the specification of flower organ identity and the regulation of floral organogenesis (Jofuku et al., *Plant Cell* 6:1211–1225, 1994); (2) establishment of flower meristem identity (Irish and Sussex, *Plant Cell* 2[8]:741–753, 1990); and (3) the temporal and spatial regulation of flower homeotic gene activity (Drews et al., *Cell* 65[6]:991–1002, 1991). DNA sequence analysis suggests that AP2 encodes a theoretical polypeptide of 432 aa, with a distinct 68 aa repeated motif termed the AP2 domain. This domain has been shown to be essential for AP2 functions and contains within the 68 aa, an eighteen amino acid core region that is predicted to form an amphipathic α-helix (Jofuku et al., *Plant Cell* 6:1211–1225, 1994). Ap2-like domain-containing transcription factors have been also been identified in both *Arabidopsis thaliana* (Okamuro et al., *Proc. Natl. Acad. Sci. USA* 94:7076–7081, 1997) and in tobacco with the identification of the ethylene responsive element binding proteins (EREBPs) (Ohme-Takagi and Shinshi, *Plant Cell* 7[2]:173–182, 1995). In Arabidopsis, these RAP2 (related to AP2) genes encode two distinct subfamilies of AP2 domain containing proteins designated AP2-like and EREBP-like (Okamuro et al., *Proc. Natl. Acad. Sci. USA* 94:7076–7081, 1997). In vitro DNA binding has not been shown to date using the RAP2 proteins; however, based upon the presence of two highly conserved motifs YRG and RAYD within the AP2 domain, it has been proposed that binding DNA binding occurs in a manner similar to that of AP2 proteins.

Zinc finger domains of the type $Cys_2His_2$ appear to represent the most abundant DNA binding motif in eukaryotic transcription factors, with several thousand being identified to date (Berg and Shi, *Science* 271[5252]:1081–1085, 1996). A structural role for zinc in transcription factors was initially proposed in 1983 for the transcription factor IIIA (TFIIIA) (Hanas et al., *J Biol. Chem.* 258[23]:14120–14125, 1983). The $Cys_2His_2$ Zinc finger domains are characterized by tandem arrays of sequences of C-x(2,4)-C-x(3)-[LIVMFYWC]-x(8)-H-x(3,5)-H (where X represents a variable amino acid). Structurally, the zinc finger consists of two antiparallel β strands followed by an a helix (Lee et al., *Science* 245[4918]:635–637, 1989). This structural arrangement allows for the cysteine and histidine side chains to coordinate the zinc with the three other conserved residues forming the hydrophobic core adjacent to the metal coordination unit (Berg and Shi, *Science* 271[5252]:1081–1085, 1996). Many proteins possessing a $Cys_2His_2$ domain have been shown to interact with DNA in a sequence-specific manner. Crystal structure analysis of the mouse transcription factor Zif268 bound to a specific DNA target indicates that the zinc fingers in the protein/DNA/DNA complex reside in the major groove of the double helix and interacts with the DNA bases through amino acid side chains referred to as the contact residues (Pavletich and Pabo, *Science* 252[5007]:809–817, 1991). The orientations of the zinc finger domains with respect to the DNA are usually identical, with each domain contacting a contiguous 3-base pair subsite, the majority of which are directed to one stand. There are few interdomain interactions and the DNA recognition by each zinc finger appears to be largely independent of the other domains (Berg and Shi, *Science* 271[5252]:1081–1085, 1996).

The CCAAT-box element identified by Gelinas et al. (*Nature* 313[6000]:323–325, 1985) has been shown to occur between 80 bp and 300 bp from the transcription start site and may operate in either orientation, with possible cooperative interactions with multiple boxes (Tasanen et al., *J Biol. Chem.* 267[16]:11513–11519, 1992); or other conserved motifs (Muro et al., *J. Biol. Chem.* 267[18]:12767–12774, 1992; Rieping and Schoffl, *Mol. Gen. Genet.* 231[2]:226–232, 1992). CCAAT-box related motifs have been identified in a number of promoters in a variety of organisms including yeast (Hahn et al., *Science* 240[4850]317–321, 1988), rat (Maity et al., *Proc. Natl. Acad. Sci. USA* 87[14]:5378–5382, 1990; Vuorio et al., *J. Biol. Chem.* 265[36]:22480–22486, 1990); and plants (Rieping and Schoffl. *Mol. Gen. Genet.* 231[2]:226–232, 1992; Kehoe et al., *Plant Cell* 6[8]:1123–1134, 1994). In both yeast and vertebrates, a protein complex has been shown to bind to the CCAAT-motif. In yeast the complex consists of three proteins, known as HAP2, HAP3 and HAP5 (Pinkham and Guarente, *Mol. Cell. Biol.* 5[12]:3410–3416, 1985).

MADS box transcription factors interact with a conserved region of DNA known as the MADS box. All MADS box transcription factors contain a conserved DNA-binding/dimerization region, known as the MADS domain, which has been identified throughout the different kingdoms (Riechmann and Meyerowitz, *Biol. Chem.* 378[10]:1079–1101, 1997). Many of the MADS box genes isolated from plants are expressed primarily in floral meristems or floral organs, and are believed to play a role in either specifying inflorescence and floral meristem identity or in determining floral organ identity. One class of regulatory genes responsible for floral meristem identity and the pattern of meristem development includes the genes APETALA1 (AP1), APETALA2 (AP2), CAULIFLOWER (CAL), LEAFY (LFY) and AGAMOUS (AG) from *Arabidopsis thaliana*. Both LFY and AP1 have been shown to encode putative transcription factors. (Weigel et al., *Cell* 69:843–859, 1992), with AP1 and AG each encoding putative transcription factors of the MADS box domain family (Yanofsky et al., *Nature* 346:35–39, 1990). Mutations in the Lfy gene have been shown to result in a partial conversion of flowers into infloresence shoots.

SUMMARY OF THE INVENTION

Briefly, the present invention provides polynucleotides isolated from plants that encode transcription factors, together with polypeptides encoded by such polynucleotides. The isolated polynucleotides and polypeptides of the present invention may be usefully employed in the modification of gene expression in plants, since both tissue- and temporal-specific gene expression patterns have been shown to be governed by transcription factors during the natural development of a plant. The inventive polynucleotides and polypeptides may thus be employed in the manipulation of plant phenotypes.

In a first aspect, the present invention provides polynucleotides isolated from eucalyptus and pine which encode transcription factors, including transcription factors from the following families of regulatory proteins: bZIP, bZIP family of G-box binding factors; basic helix-loop-helix zipper (bHLH); homeotic/homeodomain/homeobox/MADS; homeodomain zipper (ZIP); LIM domain; AP2 and EREBs; zinc finger domains of type Cys2His2; CCAAT box elements; and MYB. In specific embodiments, the isolated polynucleotides of the present invention comprise a DNA sequence selected from the group consisting of: (a) sequences recited in SEQ ID NOS: 1–591, 1183–1912 and 1931–2106; (b) complements of the sequences recited in SEQ ID NOS: 1–591, 1183–1912 and 1931–2106; (c) reverse complements of the sequences recited in SEQ ID NOS: 1–591, 1183–1912 and 1931–2106; (d) reverse sequences of the sequences recited in SEQ ID NOS: 1–591, 1183–1912 and 1931–2106; and (e) sequences having either 40%, 60%, 75%, 90% or 95% identity, as defined herein, to a sequence of (a)–(d).

In a further aspect, isolated polypeptides encoded by the inventive polynucleotides are provided. In specific embodiments, such polypeptides comprise an amino acid sequence selected from the group consisting of: (a) sequences provided in SEQ ID NOS: 592–1182, 1913–1930 and 2107–2278; and (b) polypeptides comprising sequences having either 60%, 75%, 90% or 95% identity, as defined herein, to a sequence of (a).

In another aspect, the present invention provides polypeptides isolated from eucalyptus and pine which comprise transcription factor DNA-binding domains. In specific embodiments, such polypeptides comprise an amino acid sequence selected from the group consisting of: (a) sequences provided in SEQ ID NOS: 2279–2293 and 2296–2368; and (b) sequences having either 60%, 75%, 90% or 95% identity, as defined herein, to a sequence of (a).

In a further aspect, the invention provides DNA constructs comprising a polynucleotide of the present invention, either alone, in combination with one or more other polynucleotides disclosed herein, or in combination with one or more known DNA sequences, together with transformed cells comprising such constructs.

In specific embodiments, the inventive DNA constructs comprise, in the 5'-3' direction, a gene promoter sequence; an open reading frame coding for at least a functional portion of a polypeptide encoded by an inventive polynucleotide, or a variant thereof; and a gene termination sequence. The open reading frame may be orientated in either a sense or antisense direction. DNA constructs comprising an untranslated, or non-coding, region of a polynucleotide coding for a transcription factor polypeptide of the present invention or a nucleotide sequence complementary to an untranslated region, together with a gene promoter sequence and a gene termination sequence, are also provided. Preferably, the gene promoter and termination sequences are functional in a host plant. Most preferably, the gene promoter and termination sequences are those of the original genes but others generally used in the art, such as the Cauliflower Mosaic Virus (CMV) promoter, with or without enhancers such as the Kozak sequence or Omega enhancer, and *Agrobacterium tumefaciens* nopalin synthase terminator may be usefully employed in the present invention. Tissue-specific promoters may be employed in order to target expression to one or more desired tissues. The DNA construct may further include a marker for the identification of transformed cells.

In yet a further aspect, transgenic cells comprising the DNA constructs of the present invention are provided, together with organisms, such as plants, comprising such transgenic cells. Fruits, seeds, derivatives, progeny, propagules and other products of such transgenic plants are also contemplated and encompassed by the present invention. As used herein, the term "propagule" means any part of a plant that may be used in reproduction or propagation, sexual or asexual, including cuttings.

In yet another aspect, methods for modifying gene expression in a target organism are provided, such methods including stably incorporating into the genome of the organism a DNA construct of the present invention. In a preferred embodiment, the target organism is a plant, preferably a woody plant, more preferably selected from the group consisting of eucalyptus and pine species, and most preferably from the group consisting of *Eucalyptus grandis* and *Pinus radiata*. In a related aspect, a method for producing a target organism, such as a plant, having modified gene expression is provided, the method comprising transforming a plant cell with a DNA construct of the present invention to provide a transgenic cell and cultivating the transgenic cell under conditions conducive to regeneration and mature plant growth.

The present invention further provides methods for modifying the activity of a transcription factor in a target organism, such as a plant, comprising stably incorporating into the genome of the plant a DNA construct of the present invention. In a preferred embodiment, the target plant is a woody plant, preferably selected from the group consisting of eucalyptus and pine species, and most preferably from the group consisting of *Eucalyptus grandis* and *Pinus radiata*.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

DETAILED DESCRIPTION OF THE INVENTION

The present invention provides isolated polynucleotides that encode plant transcription factors, together with isolated polypeptides encoded by such polynucleotides. As discussed above, transcription factors are components of the cellular "transcription apparatus" and are involved in the regulation of gene expression. Transcription factors are known to play a critical role in the growth and development of plants, and in cellular responses to external stimuli, such as environmental factors and disease pathogens. Transformation of plants with polynucleotides that encode proteins involved the cellular transcription process may thus be employed to modify properties such as lignin deposition, flower development, and male and female sterility.

Using the methods and materials of the present invention, the amount of a specific transcription factor may be increased or reduced by incorporating additional copies of polynucleotides, or fragments of said polynucleotides, encoding the transcription factor into the genome of a target organism, such as a plant. Similarly, an increase or decrease in the amount of the transcription factor may be obtained by transforming the target plant with antisense copies of such genes.

In one embodiment, the present invention provides isolated polynucleotides encoding, or partially encoding, plant transcription factors that are involved in the regulation of gene expression. The polynucleotides of the present invention were isolated from forestry plant sources, namely from *Eucalyptus grandis* and *Pinus radiata*, but they may alternatively be synthesized using conventional synthesis techniques. In specific embodiments, isolated polynucleotides of the present invention comprise a sequence selected from the group consisting of sequences identified as SEQ ID NOS: 1–591, 1183–1912 and 1931–2106; complements of the sequences identified as SEQ ID NOS: 1–591, 1183–1912 and 1931–2106; reverse complements of the sequences identified as SEQ ID NOS: 1–591, 1183–1912 and 1931–2106; reverse sequences of the sequences identified as SEQ ID NOS: 1–591, 1183–1912 and 1931–2106; sequences comprising at least a specified number of contiguous residues (x-mers) of any of the above-mentioned polynucleotides; extended sequences corresponding to any of the above polynucleotides; antisense sequences corresponding to any of the above polynucleotides; and variants of any of the above polynucleotides, as that term is described in this specification.

In another embodiment, the present invention provides isolated polypeptides encoded by the polynucleotides of SEQ ID NOS: 1–591, 1895–1912 and 1931–2106. In certain specific embodiments, such isolated polypeptides include a sequence selected from the group consisting of SEQ ID NOS: 592–1182, 1913–1930 and 2107–2278.

The inventive polynucleotides and polypeptides have demonstrated similarity to transformation factors that are known to be involved in regulation of transcription and/or expression in plants as shown below in Table 1.

TABLE 1

| Transcription factor family | Polynucleotide SEQ ID NO: |
|---|---|
| Basic leucine zipper (bZIP) | 133, 148, 194, 206, 246, 258, 261, 265, 279, 284, 285, 286, 290, 294, 303, 318, 331, 455, 470, 473, 497, 501, 512, 533, 538, 554, 558, 575, 1896–1899, 1938, 1939, 1950, 1958, 1959, 1961, 1963, 1969, 1973, 1981, 1983, 1989, 1991, 1998, 2002, 2004, 2021, 2022, 2025, 2028, 2029, 2033–2035, 2039, 2042, 2043, 2046, 2054, 2056, 2061, 2063, 2073, 2078, 2079, 2089, 2090, 2101, 2103, 2106 |
| bZIP family of G-box binding factors | 128, 136, 141, 142, 184, 202, 222, 244, 329, 541, 545 |
| Basic helix-loop-helix zipper | 157, 179, 223, 271, 274, 305, 317, 548, 563 |
| Myb | 138, 167, 214, 221, 232, 248, 252, 254, 255, 270, 276, 278, 280, 281, 282, 283, 292, 293, 315, 319, 328, 463, 483, 485, 486, 491, 492, 494, 502, 504, 507, 508, 510, 515, 518, 519, 520, 521, 527, 534, 536, 537, 540, 553, 559, 566, 572, 588, 1905, 1906, 1931, 1932, 1934–1936, 1940, 1948, 1949, 1951, 1953–1955, 1957, 1960, 1962, 1964–1968, 1974, 1975, 1977–1979, 1982, 1984–1988, 1992, 1994–1997, 2001, 2003, 2013–2015, 2024, 2026, 2027, 2030, 2032, 2036–2038, 2041, 2044, 2045, 2047– |

TABLE 1-continued

| Transcription factor family | Polynucleotide SEQ ID NO: |
|---|---|
| | 2049, 2051, 2052, 2057–2060, 2065, 2067, 2071, 2072, 2074–2077, 2080–2088, 2104, 2105 |
| Homeotic/homeodomain/ homeobox/MADS | 2, 3, 4, 7, 9, 10, 11, 12, 13, 17, 19, 25, 26, 27, 28, 29, 31, 32, 34, 35, 36, 37, 39, 40, 44, 45, 49, 50, 51, 52, 54, 55, 57, 60, 62, 63, 64, 65, 66, 69, 72, 74, 76, 77, 79, 82, 84, 88, 89, 92, 94, 96, 97, 98, 100, 102, 103, 104, 105, 106, 107, 108, 11, 112, 114, 116, 117, 123, 125, 127, 168, 185, 249, 250, 332, 333, 334, 336, 337, 338, 340, 341, 343, 344, 345, 346, 347, 348, 349, 350, 351, 353, 354, 355, 356, 357, 359, 360, 361, 362, 364, 365, 366, 367, 368, 370, 371, 372, 373, 374, 375, 376, 379, 380, 383, 384, 385, 386, 387, 389, 392, 393, 394, 398, 399, 400, 401, 402, 403, 406, 408, 409, 410, 412, 414, 416, 417, 418, 420, 422, 424, 425, 426, 475, 526, 529, 580, 591, 1901, 1902, 1937, 1941–1947, 1952, 1970–1972, 1976, 1980, 1990, 1993, 1999, 2000, 2006–2012, 2016–2020, 2023, 2031, 2040, 2050, 2053, 2055, 2062, 2064, 2066, 2068–2070, 2091–2100 |
| Homeodomain zipper (HDZIP) | 1, 5, 6, 14, 16, 20, 21, 22, 23, 30, 33, 41, 42, 47, 58, 59, 61, 68, 70, 71, 73, 75, 80, 86, 87, 90, 91, 93, 115, 119, 121, 126, 335, 339, 342, 352, 358, 363, 369, 377, 381, 388, 390, 396, 397, 415, 419, 421, 423, 2005, 2102 |
| LIM domain | 15, 18, 24, 43, 78, 81, 83, 198, 210, 225, 273, 378, 391, 433, 437, 450, 452 |
| AP2 and EREBs | 120, 124, 170, 171, 219, 220, 224, 226, 229, 230, 238, 242, 243, 245, 247, 256, 301, 320, 330, 432, 434, 435, 436, 445, 447, 451, 453, 454, 459, 466, 469, 476, 481, 490, 524, 546, 549, 570, 1895 |
| Zinc finger domains of type Cys2His2 | 132, 146, 154, 180, 181, 182, 183, 191, 207, 227, 234, 288, 323, 324, 325, 326, 404, 535, 567, 584, 585, 586, 587, 589, 590 |
| CCAAT box elements | 155, 174, 266, 309, 431, 460, 484, 499, 542, 551, 574, 583 |
| Other transcription factors | 8, 38, 46, 48, 53, 56, 67, 85, 95, 99, 101, 109, 110, 113, 118, 122, 129, 130, 131, 134, 135, 137, 139, 140, 143, 1444, 145, 147, 149, 150, 151, 152, 153, 156, 158, 159, 160, 161, 162, 163, 164, 165, 166, 169, 172, 173, 175, 176, 177, 178, 186, 187, 188, 189, 190, 192, 193, 195, 196, 197, 199, 200, 201, 203, 204, 205, 208, 209, 211, 212, 213, 215, 216, 217, 218, 228, 231, 233, 235, 236, 237, 239, 240, 241, 251, 253, 257, 259, 260, 262, 263, 264, 267, 268, 269, 272, 275, 277, 287, 289, 291, 295, 296, 297, 298, 299, 300, 302, 304, 306, 307, 308, 310, 311, 312, 313, 314, 316, 321, 322, 327, 382, 395, 405, 407, 411, 413, 4127, 428, 429, 430, 438, 439, 440, 441, 442, 443, 444, 446, 449, 456, 457, 458, 461, 462, 464, 465, 467, 468, 471, 472, 474, 477, 478, 479, 480, 482, 487, 488, 489, 493, 495, 496, 498, 500, 505, 506, 509, 511, 513, 514, 516, 517, 522, 523, 525, 528, 530, 531, 532, 539, 543, 544, 547, 550, 552, 555, 556, 557, 560, 561, 562, 564, 565, 568, 569, 571, 573, 577, 578, 579, 581, 582, 448, 1183–1894, 1900, 1903, 1904, 1907, 1908–1912, 1933, 1956 |

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al., "Antisense techniques," *Methods in Enzymol.* 254[23]:363–375, 1995; and Kawasaki et al., *Artific. Organs* 20[8]:836–848, 1996.

The definition of the terms "complement", "reverse complement" and "reverse sequence", as used herein, is best illustrated by the following example. For the sequence 5' AGGACC 3', the complement, reverse complement and reverse sequence are as follows:

| complement | 3' TCCTGG 5' |
| reverse complement | 3' GGTCCT 5' |
| reverse sequence | 5' CCAGGA 3'. |

The term "polypeptide", as used herein, encompasses amino acid chains of any length including full length proteins, wherein amino acid residues are linked by covalent peptide bonds. Polypeptides of the present invention may be naturally purified products, or may be produced partially or wholly using recombinant techniques. The term "polypeptide encoded by a polynucleotide" as used herein, includes polypeptides encoded by a nucleotide sequence which includes the partial isolated DNA sequences of the present invention.

All of the polynucleotides and polypeptides described herein are isolated and purified, as those terms are commonly used in the art. Preferably, the polypeptides and polynucleotides are at least about 80% pure, more preferably at least about 90% pure, and most preferably at least about 99% pure.

Some of the polynucleotides of the present invention are "partial" sequences, in that they do not represent a full length gene encoding a full length polypeptide. Such partial sequences may be extended by analyzing and sequencing various DNA libraries using primers and/or probes and well known hybridization and/or PCR techniques. Partial sequences may be extended until an open reading frame encoding a polypeptide, a full length polynucleotide and/or gene capable of expressing a polypeptide, or another useful portion of the genome is identified. Such extended sequences, including full length polynucleotides and genes, are described as "corresponding to" a sequence identified as one of the sequences of SEQ ID NOS: 1–591, 1183–1912 and 1931–2106, or a variant thereof, or a portion of one of the sequences of SEQ ID NOS: 1–591, 1183–1912 and 1931–2106, or a variant thereof, when the extended polynucleotide comprises an identified sequence or its variant, or an identified contiguous portion (x-mer) of one of the sequences of SEQ ID NOS: 1–591, 1183–1912 and 1931–2106, or a variant thereof. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Similarly, RNA sequences, reverse sequences, complementary sequences, antisense sequences, and the like, corresponding to the polynucleotides of the present invention, may be routinely ascertained and obtained using the cDNA sequences identified as SEQ ID NOS: 1–591, 1183–1912 and 1931–2106.

The polynucleotides identified as SEQ ID NOS: 1–591, 1183–1912 and 1931–2106 may contain open reading frames ("ORFs") or partial open reading frames encoding polypeptides. Open reading frames may be identified using techniques that are well known in the art. These techniques include, for example, analysis for the location of known start and stop codons, most likely reading frame identification based on codon frequencies, etc. Suitable tools and software for ORF analysis are available, for example, on the Internet. Additional tools and software for ORF analysis include GeneWise, available from The Sanger Center, Wellcome Trust Genome Campus, Hinxton, Cambridge, CB10 1SA, United Kingdom; Diogenes, available from Computational Biology Centers, University of Minnesota, Academic Health Center, UMHG Box 43 Minneapolis Minn. 55455; and GRAIL, available from the Informatics Group, Oak Ridge National Laboratories, Oak Ridge, Tennessee Tenn. Open reading frames and portions of open reading frames may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, open reading frames encoding polypeptides may be identified using the polynucleotides of the present invention.

Once open reading frames are identified in the polynucleotides of the present invention, the open reading frames may be isolated and/or synthesized. Expressible DNA constructs comprising the open reading frames and suitable promoters, initiators, terminators, etc., which are well known in the art, may then be constructed. Such DNA constructs may be introduced into a host cell to express the polypeptide encoded by the open reading frame. Suitable host cells may include various prokaryotic and eukaryotic cells, including plant cells, mammalian cells, bacterial cells, algae and the like.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences, (polynucleotide or polypeptide) preferably exhibit at least 50%, more preferably at least 75%, more preferably at least 90% and most preferably at least 95% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100. By way of illustration only, assume an inventive polynucleotide having 220 nucleotides has a hit to a polynucleotide sequence in the EMBL database having 520 nucleotides over a stretch of 23 nucleotides in the alignment produced by the BLASTN algorithm using the parameters described above. The 23 nucleotide region includes 21 identical nucleotides, one gap and one different nucleotide. The percentage identity of the inventive polynucleotide to the hit in the EMBL library is thus 21/220 times 100, or 9.5%. The polynucleotide sequence in the EMBL database is thus not a variant of the inventive polynucleotide.

Polynucleotide and polypeptide sequences may be aligned, and percentage of identical residues in a specified region may be determined against another polynucleotide or polypeptide sequence, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP algorithm. The BLASTN, BLASTX and BLASTP programs are available on the NCBI anonymous FTP server under/blast/executables, and from the National Center for Biotechnology Information (NCBI) National Library of Medicine, Building 38A, Room 8N805, Bethesda, Md. 20894, USA. The BLASTN algorithm Version 2.0.4 [Feb. 24, 1998] and Version 2.0.6 [Sep. 16, 1998], set to the default parameters described in the documentation and distributed with the algorithm, are preferred for use in the determination of polynucleotide variants according to the present invention. The BLASTP algorithm, is preferred for use in the determination of polypeptide variants according to the present invention. The use of the BLAST family of algorithms, including BLASTN, BLASTP, and BLASTX, is described at NCBI's Internet website and in the publication of Altschul et al., *Nucleic Acids Res.* 25:3389–3402, 1997.

The computer algorithm FASTA is available on the Internet, and from the University of Virginia by contacting David Hudson, Assistance Provost for Research, University of Virginia, PO Box 9025, Charlottesville, Va. Version 2.0u4 [February 1996], set to the default parameters described in the documentation and distributed with the algorithm, may be used in the determination of variants according to the present invention. The use of the FASTA algorithm is described in Pearson and Lipman, *Proc. Natl. Acad. Sci. USA* 85:2444–2448, 1988; and Pearson, *Methods in Enzymol.* 183:63–98, 1990.

The following running parameters are preferred for determination of alignments and similarities using BLASTN that contribute to the E values and percentage identity for polynucleotide sequences: Unix running command: blastall -p blastn -d embldb -e 10-G0-E0 -r 1 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; and -o Blast report Output File [File Out] Optional.

The following running parameters are preferred for determination of alignments and similarities using BLASTP that contribute to the E values and percentage identity of polypeptide sequences: blastall -p blastp -d swissprotdb -e 10 -G 0 -E 0 -v 30 -b 30 -i queryseq -o results; wherein the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described above.

Alternatively, variant polynucleotides of the present invention hybridize to the polynucleotide sequences recited in SEQ ID NOS: 1–591, 1183–1912 and 1931–2106, or complements, reverse sequences, or reverse complements of those sequences, under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1 % SDS at 65° C.

The present invention also encompasses polynucleotides that differ from the disclosed sequences but that, as a consequence of the degeneracy of the genetic code, encode a polypeptide which is the same as that encoded by a polynucleotide of the present invention. Thus, polynucleotides comprising sequences that differ from the polynucleotide sequences recited in SEQ ID NOS: 1–591, 1183–1912 and 1931–2106; or complements, reverse sequences, or reverse complements thereof, as a result of conservative substitutions are contemplated by and encompassed within the present invention. Additionally, polynucleotides comprising sequences that differ from the polynucleotide sequences recited in SEQ ID NOS: 1–591, 1183–1912 and 1931–2106, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences recited in SEQ ID NOS: 592–1182, 1913–1930 and 2107–2278, as a result of amino acid substitutions, insertions, and/or deletions totaling less than 10% of the total sequence length are contemplated by and encompassed within the present invention. In certain embodiments, variants of the inventive polypeptides possess biological activities that are the same or similar to those of the inventive polypeptides. Such variant polypeptides function as transcription factors and are thus capable of modifying gene expression in a plant. Similarly, variant polynucleotides may encode polypeptides that function as transcription factors.

In addition to having a specified percentage identity to an inventive polynucleotide or polypeptide sequence, variant polynucleotides and polypeptides preferably have additional structure and/or functional features in common with the inventive polynucleotide or polypeptide. Polypeptides having a specified degree of identity to a polypeptide of the present invention share a high degree of similarity in their primary structure and have substantially similar functional properties. In addition to sharing a high degree of similarity in their primary structure to polynucleotides of the present invention, polynucleotides having a specified degree of identity to, or capable of hybridizing to an inventive polynucleotide preferably have at least one of the following features: (i) they contain an open reading frame or partial open reading frame encoding a polypeptide having substantially the same functional properties as the polypeptide encoded by the inventive polynucleotide; or (ii) they contain identifiable domains in common.

Polynucleotides of the present invention also comprehend polynucleotides comprising at least a specified number of contiguous residues (x-mers) of any of the polynucleotides identified as SEQ ID NOS: 1–591, 1183–1912 and 1931–2106, complements, reverse sequences, and reverse complements of such sequences, and their variants. Similarly, polypeptides of the present invention comprehend polypeptides comprising at least a specified number of contiguous residues (x-mers) of any of the polypeptides identified as SEQ ID NOS: 592–1182, 1913–1930 and 2107–2278, and their variants. As used herein, the term "x-mer," with reference to a specific value of "x," refers to a sequence comprising at least a specified number ("x") of contiguous residues of any of the polynucleotides identified as SEQ ID NOS: 1–591, 1183–1912 and 1931–2106, or the polypeptides identified as SEQ ID NOS: 592–1182, 1913–1930 and 2107–2278. According to preferred embodiments, the value of x is preferably at least 20, more preferably at least 40, more preferably yet at least 60, and most preferably at least 80. Thus, polynucleotides and polypeptides of the present invention comprise a 20-mer, a 40-mer, a 60-mer, an 80-mer, a 100-mer, a 120-mer, a 150-mer, a 180-mer, a 220-mer, a 250-mer, a 300-mer, a 400-mer, a 500-mer or a 600-mer of a polynucleotide or polypeptide identified as SEQ ID NOS: 1–2368, and variants thereof.

The inventive polynucleotides may be isolated by high throughput sequencing of cDNA libraries prepared from *Eucalyptus grandis* and *Pinus radiata* as described below in Examples 1 and 2. Alternatively, oligonucleotides based on the sequences provided in SEQ ID NOS: 1–591, 1183–1912 and 1931–2106 may be prepared as detailed below and used to identify positive clones in either cDNA or genomic DNA libraries from *Eucalyptus grandis* and *Pinus radiata* by means of hybridization or PCR techniques. Probes may be shorter than the sequences provided herein but should be at least about 10, preferably at least 15, and most preferably at least about 20 nucleotides in length. Hybridization and PCR techniques suitable for use with such oligonucleotides are well known in the art, and include those taught by Sambrook et al., Ibid. Positive clones may be analyzed by restriction enzyme digestion, DNA sequencing or the like.

The polynucleotides of the present invention may alternatively be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be sized entirely in vitro.

In certain embodiments, the DNA constructs of the present invention include an open reading frame coding for at least a functional portion of a polypeptide of the present invention or a variant thereof. As used herein, the "functional portion" of a polypeptide is that portion which contains the active site essential for regulating gene expression, i.e., the portion of the molecule that is capable of binding to, or interacting with, the promoter of the gene to be expressed. The DNA-binding domain(s) for certain of the inventive polypeptides are identified below in Table 2. These DNA binding domains were identified using PROSITE 15.0 pattern or profile sequences as listed in the PROSITE database. PROSITE is available on the Internet and its use is described in Hofman et al., *Nucleic Acids Res.* 27:215–219, 1999; and in Bairoch, *Nucleic Acids Res.* 20:Suppl.2013–2018, 1992.

TABLE 2

| Polynucleotide SEQ ID NO: | DNA-binding Domain(s) SEQ ID NO: |
| --- | --- |
| 1931 | 2283 |
| 1934 | 2284, 2285 |
| 1940 | 2288 |
| 1949 | 2293 |
| 1951 | 2279, 2280 |
| 1953 | 2296, 2297 |

TABLE 2-continued

| Polynucleotide SEQ ID NO: | DNA-binding Domain(s) SEQ ID NO: |
|---|---|
| 1957 | 2298 |
| 1960 | 2301, 2302 |
| 1962 | 2307 |
| 1965 | 2308, 2309 |
| 1967 | 2281, 2282 |
| 1978 | 2320 |
| 1979 | 2321 |
| 1982 | 2322, 2323 |
| 1986 | 2324 |
| 1992 | 2335 |
| 1994 | 2336, 2337 |
| 1995 | 2338, 2339 |
| 1997 | 2340 |
| 2003 | 2286, 2287 |
| 2013 | 2289, 2290 |
| 2020 | 2291, 2292 |
| 2027 | 2299, 2300 |
| 2030 | 2303, 2304 |
| 2032 | 2305, 2306 |
| 2036 | 2310, 2311 |
| 2038 | 2312, 2313 |
| 2049 | 2314, 2315 |
| 2051 | 2316, 2317 |
| 2052 | 2318, 2319 |
| 2057 | 2325, 2326 |
| 2059 | 2327, 2328 |
| 2060 | 2329, 2330 |
| 2065 | 2331, 2332 |
| 2067 | 2333, 2334 |
| 2074 | 2342, 2343 |
| 2075 | 2344, 2345 |
| 2076 | 2346, 2347 |
| 2077 | 2348, 2349 |
| 2080 | 2352 |
| 2081 | 2353 |
| 2082 | 2354 |
| 2083 | 2355, 2356 |
| 2084 | 2357, 2358 |
| 2085 | 2359, 2360 |
| 2086 | 2361, 2362 |
| 2087 | 2365, 2366 |
| 2088 | 2367, 2368 |
| 2104 | 2350, 2351 |
| 2105 | 2363, 2364 |

The functional portion of a polypeptide may also be determined by targeted mutagenesis and screening of modified protein products with protocols well known in the art (Solano et al., *J. Biol. Chem.* 272:2889–95, 1997). The active site will generally exhibit high substrate specificity. Portions of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2154, 1963. Equipment for automated synthesis of polypeptides is commercially available from suppliers such as Perkin Elmer/Applied BioSystems, Inc. (Foster City, Calif.), and may be operated according to the manufacturer's instructions.

An open reading frame may be inserted in the DNA construct in a sense or antisense orientation, such that transformation of a target plant with the DNA construct will lead to a change in the amount of polypeptide compared to the wild-type plant. Transformation with a DNA construct comprising an open reading frame in a sense orientation will generally result in over-expression of the selected gene, while transformation with a DNA construct comprising an open reading frame in an antisense orientation will generally result in reduced expression of the selected gene. A population of plants transformed with a DNA construct comprising an open reading frame of the present invention in either a sense or antisense orientation may be screened for increased or reduced expression of the gene in question using techniques well known to those of skill in the art, and plants having the desired phenotypes may thus be isolated.

Alternatively, expression of a gene encoding a plant transcription factor may be inhibited by inserting a portion of an open reading frame of the present invention, in either sense or antisense orientation, in the DNA construct. Such portions need not be full-length but preferably comprise at least 25 and more preferably at least 50 residues of an inventive DNA sequence. A much longer portion or even the full length DNA corresponding to the complete open reading frame may be employed. The portion of the open reading frame does not need to be precisely the same as the endogenous sequence, provided that there is sufficient sequence similarity to achieve inhibition of the target gene. Thus a sequence derived from one species may be used to inhibit expression of a gene in a different species. A population of plants transformed with a genetic construct comprising an open reading frame of the present invention in either a sense or antisense orientation may be screened for increased or reduced expression of the gene in question using techniques well known to those of skill in the art, and plants having the desired phenotypes may thus be isolated.

In another embodiment, the inventive DNA constructs comprise a DNA sequence including an untranslated, or non-coding, region of a gene coding for a polypeptide of the present invention, or a DNA sequence complementary to such an untranslated region. Examples of untranslated regions which may be usefully employed in such constructs include introns and 5'-untranslated leader sequences. Transformation of a target plant with such a DNA construct may lead to a reduction in the amount of the polypeptide expressed in the plant by the process of cosuppression, in a manner similar to that discussed, for example, by Napoli et al. (*Plant Cell* 2:279–290, 1990), and de Carvalho Niebel et al. (Plant Cell 7:347–358, 1995).

Alternatively, regulation of polypeptide expression can be achieved by inserting appropriate sequences or subsequences (e.g. DNA or RNA) in ribozyme constructs (McIntyre and Manners, *Transgenic Res.* 5[4]:257–262, 1996). Ribozymes are synthetic RNA molecules that comprise a hybridizing region complementary to two regions, each of which comprises at least 5 contiguous nucleotides in a mRNA molecule encoded by one of the inventive polynucleotides. Ribozymes possess highly specific endonuclease activity, which autocatalytically cleaves the mRNA.

The DNA constructs of the present invention further comprise a gene promoter sequence and a gene termination sequence, operably linked to the DNA sequence to be transcribed, which control expression of the gene. The gene promoter sequence is generally positioned at the 5' end of the DNA sequence to be transcribed, and is employed to initiate transcription of the DNA sequence. Gene promoter sequences are generally found in the 5' untranslated region of a gene but they may exist downstream of the open reading frame, in introns (Luehrsen, *Mol. Gen. Genet.* 225:81–93, 1991) or in the coding region, as for example in a plant defence gene (Douglas et al., *EMBO J.* 10:1767–1775, 1991). When the construct includes an open reading frame in a sense orientation, the gene promoter sequence also initiates translation of the open reading frame. For DNA constructs comprising either an open reading frame in an antisense orientation or an untranslated region, the gene promoter sequence may consist only of a transcription initiation site having a RNA polymerase binding site.

A variety of gene promoter sequences which may be usefully employed in the DNA constructs of the present invention are well known in the art. The gene promoter sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or antisense RNA only in the tissue of interest. With DNA constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as eucalyptus or pine are used. Other examples of gene promoters which may be usefully employed in the present invention include mannopine synthase (mas), octopine synthase (ocs) and those reviewed by Chua et al. (*Science* 244:174–181, 1989).

The gene termination sequence, which is located 3' to the DNA sequence to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original gene or from the target species to be transformed.

The DNA constructs of the present invention may also contain a selection marker that is effective in cells of the target organism, such as a plant, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach, A and Weissbach H, eds., *Methods for Plant Molecular Biology*, Academic Press Inc.: San Diego, Calif., 1988). Transformed cells can thus be identified by their ability to grow in media containing the antibiotic in question. Alternatively, the presence of the desired construct in transformed cells can be determined by means of other techniques well known in the art, such as Southern and Western blots.

A transcription initiation site is additionally included in the DNA construct when the sequence to be transcribed lacks such a site.

Techniques for operatively linking the components of the inventive DNA constructs are well known in the art and include the use of synthetic linkers containing one or more restriction endonuclease sites as described, for example, by Sambrook et al., (*Molecular cloning: a laboratory manual*, CSHL Press: Cold Spring Harbor, N.Y., 1989). The DNA construct of the present invention may be linked to a vector having at least one replication system, for example *E. coli*, whereby after each manipulation, the resulting construct can be cloned and sequenced and the correctness of the manipulation determined.

The DNA constructs of the present invention may be used to transform a variety of target organisms including, but not limited to, plants. Plants which may be transformed using the inventive constructs include both monocotyledonous angiosperms (e.g., grasses, corn, grains, oat, wheat and barley); and dicotyledonous angiosperms (e.g., Arabidopsis, tobacco, legumes, alfalfa, oaks, eucalyptus, maple); and Gymnosperms (e.g., Scots pine (Aronen, *Finnish Forest Res. Papers*, Vol. 595, 1996); white spruce (Ellis et al., *Biotechnology* 11:84–89, 1993); and larch (Huang et al., *In Vitro Cell* 27:201–207, 1991). In a preferred embodiment, the inventive DNA constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. Other species which may be usefully transformed with the DNA constructs of the present invention include, but are not limited to; pines such as *Pinus banksiana, Pinus brutia, Pinus caribaea, Pinus clausa, Pinus contorta, Pinus coulteri, Pinus echinata, Pinus eldarica, Pinus ellioti, Pinus jefreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana;* other gymnosperms, such as *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata;* and Eucalypts, such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nichoiji, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus*

*torelliana, Eucalyptus urnigera, Eucalyptus urophylla, Eucalyptus viminalis, Eucalyptus viridis, Eucalyptus wandoo* and *Eucalyptus youmanni;* and hybrids of any of these species.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by Agrobacterium Ti plasmid technology, as described, for example by Bevan (*Nucleic Acids Res.* 12:8711–8721, 1984). Targets for the introduction of the DNA constructs of the present invention include tissues, such as leaf tissue, dissociated cells, protoplasts, seeds, embryos, meristematic regions; cotyledons, hypocotyls, and the like. The preferred method for transforming eucalyptus and pine is a biolistic method using pollen (see, for example, Aronen, in *Finnish Forest Res. Papers* 595:53, 1996) or easily regenerable embryonic tissues.

Once the cells are transformed, cells having the inventive DNA construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., "Somatic embryogenesis in woody plants," in Thorpe TA, ed., *In vitro embryogenesis of plants* (Current Plant Science and Biotechnology in Agriculture, 20[12]:471–540, 1995. Specific protocols for the regeneration of spruce are discussed by Roberts et al. ("Somatic embryogenesis of spruce," in Redenbaugh K, ed., *Synseed: applications of synthetic seed to crop improvement,* CRC Press: 23:427449, 1993). Transformed plants having the desired phenotype may be selected using techniques well known in the art. The resulting transformed plants may be reproduced sexually or asexually, using methods well known in the art, to give successive generations of transgenic plants.

As discussed above, the production of RNA in target cells can be controlled by choice of the promoter sequence, or by selecting the number of functional copies or the site of integration of the DNA sequences incorporated into the genome of the target host. A target organism may be transformed with more than one DNA construct of the present invention, thereby modulating the activity of more than one transcription factor, for example affecting gene expression in more than one tissue, or at more than one time in the development of the target organism. Similarly, a DNA construct may be assembled containing more than one open reading frame coding for a polypeptide of the present invention or more than one untranslated region of a gene coding for such a polypeptide. The polynucleotides of the present inventive may also be employed in combination with other known sequences encoding transcription factors.

Polynucleotide probes and primers complementary to and/or corresponding to SEQ ID NOS: 1–591, 1183–1912 and 1931–2106, and variants of those sequences, are also comprehended by the present invention. Such oligonucleotide probes and primers are substantially complementary to the polynucleotide of interest. As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction. An oligonucleotide probe or primer is described as "corresponding to" a polynucleotide of the present invention, including one of the sequences set out as SEQ ID NOS: 1–591, 1183–1912 and 1931–2106, or a variant, if the oligonucleotide probe or primer, or its complement, is contained within one of the sequences set out as SEQ ID NOS: 1–591, 1183–1912 and 1931–2106, or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. The DNA from plants or samples or products containing plant material can be either genomic DNA or DNA derived by preparing cDNA from the RNA present in the sample.

In addition to DNA-DNA hybridization, DNA-RNA or RNA-RNA hybridization assays are also possible. In the first case, the mRNA from expressed genes would then be detected instead of genomic DNA or cDNA derived from mRNA of the sample. In the second case, RNA probes could be used. In addition, artificial analogs of DNA hybridizing specifically to target sequences could also be used.

In specific embodiments, the oligonucleotide probes and/or primers comprise at least about contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA-DNA hybridization stringencies, annealing and melting temperatures, and potential for formation of loops and other factors, which are well known in the art. Tools and software suitable for designing probes, and especially suitable for designing PCR primers, are available on the Internet, for example. A software program suitable for designing probes, and especially for designing PCR primers, is available from Premier Biosoft International, 3786 Corina Way, Palo Alto, Calif. 94303–4504. Preferred techniques for designing PCR primers are also disclosed in Dieffenbach and Dyksler, *PCR primer: a laboratory manual,* CSHL Press: Cold Spring Harbor N.Y. 1995.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NOS: 1–591, 1183–1912 and 1931–2106.

In one embodiment useful for high-throughput assays, the oligonucleotide probe kits of the present invention comprise multiple probes in an array format, wherein each probe is immobilized in a predefined, spatially addressable location on the surface of a solid substrate. Array formats which may be usefully employed in the present invention are disclosed, for example, in U.S. Pat. Nos. 5,412,087, 5,545,531, and PCT Publication No. WO 95/00530, the disclosures of which are hereby incorporated by reference.

The significance of high-throughput screening systems is apparent for applications such as plant breeding and quality control operations in which there is a need to identify large numbers of seed lots and plant seedlings, to examine samples or products for unwanted plant materials, to identify plants or samples or products containing plant material for quarantine purposes etc. or to ascertain the true origin of plants or samples or products containing plant material. Screening for the presence or absence of polynucleotides of the present invention used as identifiers for tagging plants is valuable for later detecting the amount of gene flow in plant breeding, introgression of genes via dispersed pollen, etc.

In this manner, oligonucleotide probe kits of the present invention may be employed to examine the presence/absence (or relative amounts in case of mixtures) of polynucleotides of the present invention in different samples or products containing different materials rapidly and in a cost-effective manner. Examples of plant species that may be examined using the present invention, include forestry species, such as pine and eucalyptus species, other tree species, agricultural plants including crop and forage plants, and horticultural plants.

Another aspect of the present invention involves collections of polynucleotides of the present invention. A collection of polynucleotides of the present invention, particularly the polynucleotides identified as SEQ ID NOS: 1–591, 1183–1912 and 1931–2106, and variants and x-mers thereof, may be recorded and/or stored on a storage medium and subsequently accessed for purposes of analysis, comparison, etc. Suitable storage media include magnetic media such as magnetic diskettes, magnetic tapes, CD-ROM storage media, optical storage media, and the like. Suitable storage media and methods for recording and storing information, as well as accessing information such as polynucleotide sequences recorded on such media, are well known in the art. The polynucleotide information stored on the storage medium is preferably computer-readable and may be used for analysis and comparison of the polynucleotide information.

Another aspect of the present invention thus involves storage medium on which are recorded a collection of the polynucleotides of the present invention, particularly a collection of the polynucleotides identified as SEQ ID NOS: 1–591, 1183–1912 and 1931–2106, and variants thereof, as well as x-mers of the polynucleotides of SEQ ID NOS: 1–591, 1183–1912 and 1931–2106, and extended sequences, probes and primers comprising or corresponding to a polynucleotide of SEQ ID NOS: 1–591, 1183–1912 and 1931–2106. According to one embodiment, the storage medium includes a collection of at least 20, preferably at least 50, more preferably at least 100, and most preferably at least 200 of the polynucleotides of the present invention, preferably the polynucleotides identified as SEQ ID NOS: 1–591, 1183–1912 and 1931–2106, or variants of such polynucleotides.

The following examples are offered by way of illustration and not by way of limitation.

EXAMPLE 1

Isolation and Characterization of cDNA Clones from *Eucalyptus grandis*

Nine *Eucalyptus grandis* cDNA expression libraries (prepared from either mature shoot buds, early wood phloem, floral tissue, leaf tissue (two independent libraries), feeder roots, structural roots, xylem or early wood xylem) were constructed and screened as follows.

Total RNA was extracted from the plant tissue using the protocol of Chang et al. (*Plant Molecular Biology Reporter* 11:113–116, 1993). mRNA was isolated from the total RNA preparation using either a Poly(A) Quik mRNA Isolation Kit (Stratagene, La Jolla, Calif.) or Dynal Beads Oligo $(dT)_{25}$ (Dynal, Skogen, Norway). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) using an aliquot (1–5 $\mu$l) from the 5 $\mu$l ligation reaction dependent upon the library. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequence for positive clones was obtained using a Perkin Elmer/Applied Biosystems Division Prism 377 sequencer. cDNA clones were sequenced first from the 5' end and, in some cases, also from the 3' end. For some clones, internal sequence was obtained using either Exonuclease III deletion analysis, yielding a library of differentially sized subclones in pBK-CMV, or by direct sequencing using gene-specific primers designed to identified regions of the gene of interest.

The determined cDNA sequences were compared to known sequences in the EMBL database (up to mid-July 1999) using the computer algorithms FASTA and/or BLASTN. Multiple alignments of redundant sequences were used to build up reliable consensus sequences. The determined cDNA sequences are provided in SEQ ID NOS: 1–331, 1183–1536, 1896–1901, 1905, 1906, 1908–1910, 1932–1968, 2001–2036, 2074–2079 and 2104. Based on similarity to known sequences from other plant species, the isolated DNA sequences were identified as encoding transcription factors, as detailed in Table 1 above. The predicted amino acid sequences corresponding to the DNA sequences of SEQ ID NOS: 1–331, 1896–1901, 1905, 1906, 1908, 1909, 1910, 1932–1968, 2001–2036, 2074–2079 and 2104 are provided in SEQ ID NOS: 592–922, 1914–1919, 1923, 1924, 1926–1928, 2108–2142, 2175–2210, 2247–2252 and 2276, respectively.

EXAMPLE 2

Isolation and Characterization of cDNA Clones from *Pinus radiata*

Fourteen *Pinus radiata* cDNA expression libraries (prepared from either shoot bud tissue, suspension cultured cells, early wood phloem (two independent libraries), fascicle meristem tissue, male strobilus, root (unknown lineage), feeder roots, structural roots, female strobilus, cone primordia, female receptive cones and xylem (two independent libraries)) were constructed and screened as described above in Example 1.

DNA sequence for positive clones was obtained using forward and reverse primers on a Perkin Elmer/Applied Biosystems Division Prism 377 sequencer and the determined sequences were compared to known sequences in the database as described above.

Based on similarity to known sequences from other plant species, the isolated DNA sequences (SEQ ID NOS: 332–591, 1537–1894, 1895, 1902–1904, 1907, 1911, 1912, 1931, 1969–2000, 2037–2073, 2080–2103, 2105 and 2106) were identified as encoding transcription factors as detailed above in Table 1. The predicted amino acid sequences corresponding to the DNA sequences of SEQ ID NOS: 332–591, 1895, 1902–1904, 1907, 1911, 1912, 1931, 1969–2000, 2037–2073, 2080–2103, 2105 and 2106 are provided in SEQ ID NOS: 923–1182, 1913, 1920–1922, 1925, 1929–1930, 2107, 2143–2174, 2211–2246, 2253–2275, 2277 and 2278, respectively.

EXAMPLE 3

Use of a Myb Transcription Factor Gene to Modify Gene Expression in Plants

Transformation of tobacco plants with a *Eucalyptus grandis* Myb transcription factor gene is performed as follows. DNA constructs comprising sense and anti-sense constructs containing a DNA sequence including the coding region of the Myb transcription factor of SEQ ID NO: 2076 are constructed and inserted into *Agrobacterium tumefaciens* by direct transformation using published methods (see An G, Ebert P R, Mitra A, Ha S B, "Binary vectors," in Gelvin S B and Schilperoort R A, eds., *Plant Molecular Biology Manual*, Kluwer Academic Publishers: Dordrecht, 1988). The constructs of sense DNAs are made by direct cloning from PBK-CMV plasmid by cloning cDNA insert into pART7 plasmid, which is then cut by NotI enzyme and 35S-Insert-OCS 3' UTR put into pART27 plant expression vector (see Gleave, *Plant Molecular Biology* 20:1203–1207, 1992). The presence and integrity of the transgenic constructs are verified by restriction digestion and DNA sequencing.

Tobacco (*Nicotiana tabacum* cv. *Samsun*) leaf sections are transformed with the sense and anti-sense constructs using the method of Horsch et al. (*Science* 227:1229–1231, 1985). *Arabidopsis thaliana* (ecotype: Columbia) whole plants are transformed with the sense and anti-sense constructs using either the vacuum infiltration (Bechtold et al., *C. R. Acad.* 316:1194–1199, 1992), or floral dip (Clough and Bent, *The Plant Journal* 16:735–743, 1998) procedures. Transformed plants containing the appropriate construct are verified using Southern blot experiments. Expression of the Eucalyptus Myb transcription factor gene in transformed plants is confirmed by isolating total RNA from each independent transformed plant line created with the Myb transcription factor gene sense and anti-sense constructs. The RNA samples are analysed in Northern blot experiments to determine the level of expression of the transgene in each transformed line. The expression level of the Myb transcription factor, encoded by the Eucalyptus Myb transcription factor gene and by the endogenous Myb transcription factor gene, for each transformed plant line created with the sense and anti-sense constructs is compared to that of wild-type control plants.

SEQ ID NOS: 1–2368 are set out in the attached Sequence Listing. The codes for nucleotide and amino acid sequences used in the attached Sequence Listing, including the symbols "n" and "Xaa", conform to WIPO Standard ST.25 (1998), Appendix 2, Table 1.

Although the present invention has been described in some detail by way of illustration and example for purposes of clarity of understanding, changes and modifications can be carried out without departing from the scope of the invention which is intended to be limited only by the scope of the claims.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6833446B1). An electronic copy of the "Sequence Listing" will also be available from the USPTO upon request and payment of the fee set forth in 37 CFR 1.19(b)(3).

What is claimed is:

1. An isolated polynucleotide that encodes a polypeptide comprising a sequence selected from the group consisting of SEQ ID NO: 2346 and 2347.

2. A DNA construct comprising a polynucleotide sequence selected from the group consisting of:
    (a) SEQ ID NO: 2076; and
    (b) sequences that are degeneratively equivalent to SEQ ID NO: 2076, wherein the sequence encodes a Myb transcription factor.

3. A DNA construct comprising, in the 5'–3' direction:
    (a) a gene promoter sequence,
    (b) an open reading frame of an isolated polynucleotide comprising a sequence selected from the group consisting of:
        (i) SEQ ID NO: 2076; and
        (ii) sequences that are degeneratively equivalent to SEQ ID NO: 2076, wherein the sequence encodes a Myb transcription factor; and
    (c) a gene termination sequence.

4. The DNA construct of claim 3 wherein the open reading frame is in a sense orientation.

5. The DNA construct of claim 3 wherein the open reading frame is in an antisense orientation.

6. The DNA construct of claim 3 wherein the gene promoter sequence and gene termination sequences are functional in a plant host.

7. The DNA construct of claim 3 further comprising a marker for identification of transformed cells.

8. A DNA construct comprising in the 5'–3' direction:
    (a) a gene promoter sequence,
    (b) an untranslated region of an isolated polynucleotide comprising a sequence selected from the group consisting of:
        (i) SEQ ID NO: 2076; and
        (ii) sequences that are degeneratively equivalent to SEQ ID NO: 2076, wherein the sequence encodes a Myb transcription factor; and
    (c) a gene termination sequence.

9. The DNA construct of claim 8 wherein the untranslated region is in a sense orientation.

10. The DNA construct of claim 8 wherein the untranslated region is in an antisense orientation.

11. The DNA construct of claim 8 wherein the gene promoter sequence and gene termination sequence are functional in a plant host.

12. An isolated polynucleotide comprising SEQ ID NO: 2076.

13. An isolated polynucleotide comprising a sequence that is degeneratively equivalent to SEQ ID NO: 2076 wherein the polynucleotide encodes a Myb transcription factor.

14. An isolated polynucleotide comprising a sequence selected from the group consisting of:
    (a) nucleotide sequences that are 200-mers of SEQ ID NO: 2076;
    (b) nucleotide sequences that are 100-mers of SEQ ID NO: 2076; and
    (c) nucleotide sequences that are 40-mers of SEQ ID NO: 2076.

* * * * *